(12) United States Patent
Heaton et al.

(10) Patent No.: US 9,198,889 B2
(45) Date of Patent: *Dec. 1, 2015

(54) METHODS FOR TREATING POST-TRAUMATIC STRESS DISORDER

(71) Applicant: Basic Research L.L.C., Salt Lake City, UT (US)

(72) Inventors: Amy L. Heaton, Salt Lake City, UT (US); Mitchell K. Friedlander, Salt Lake City, UT (US); Dennis Gay, Salt Lake City, UT (US)

(73) Assignee: QUALITY IP HOLDINGS, LLC, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/623,101

(22) Filed: Sep. 19, 2012

(65) Prior Publication Data

US 2014/0079823 A1    Mar. 20, 2014

(51) Int. Cl.
| | |
|---|---|
| A61K 36/53 | (2006.01) |
| A61K 31/198 | (2006.01) |
| A61K 31/4015 | (2006.01) |
| A61K 36/538 | (2006.01) |
| A23L 1/00 | (2006.01) |

(52) U.S. Cl.
CPC ............ *A61K 31/198* (2013.01); *A23L 1/00* (2013.01); *A61K 31/4015* (2013.01); *A61K 36/538* (2013.01)

(58) Field of Classification Search
None
See application file for complete search history.

(56) References Cited

U.S. PATENT DOCUMENTS

| | | | |
|---|---|---|---|
| 4,224,316 A | 9/1980 | Momany | |
| 6,071,926 A | 6/2000 | Van Cauter et al. | |
| 6,346,264 B1 | 2/2002 | White | |
| 6,368,617 B1 | 4/2002 | Hastings et al. | |
| 6,517,832 B1 * | 2/2003 | Marrongelle et al. | 424/93.45 |
| 6,974,841 B1 | 12/2005 | Rapisarda | |
| 7,790,683 B2 | 9/2010 | Grasso et al. | |
| 8,551,542 B1 | 10/2013 | Heaton et al. | |
| 8,715,752 B2 | 5/2014 | Heaton et al. | |
| 8,722,114 B2 | 5/2014 | Heaton et al. | |
| 8,722,115 B2 | 5/2014 | Heaton et al. | |
| 8,734,864 B2 | 5/2014 | Heaton et al. | |
| 8,747,921 B2 | 6/2014 | Heaton et al. | |
| 8,747,922 B2 | 6/2014 | Heaton et al. | |
| 8,747,923 B2 | 6/2014 | Heaton et al. | |
| 8,765,195 B2 | 7/2014 | Heaton et al. | |
| 2002/0165343 A1 | 11/2002 | Martinez et al. | |
| 2003/0068309 A1 | 4/2003 | De Simone | |
| 2004/0063608 A1 | 4/2004 | Mowrey et al. | |
| 2004/0122234 A1 | 6/2004 | Hauser et al. | |
| 2007/0286909 A1 | 12/2007 | Smith et al. | |
| 2008/0050777 A1 | 2/2008 | Buechler et al. | |
| 2010/0047364 A1 | 2/2010 | Moneymaker et al. | |
| 2010/0186121 A1 | 7/2010 | Unkefer et al. | |
| 2011/0052754 A1 | 3/2011 | Foley | |
| 2011/0081329 A1 | 4/2011 | Smith et al. | |
| 2014/0079822 A1 | 3/2014 | Heaton et al. | |
| 2014/0079830 A1 | 3/2014 | Heaton et al. | |
| 2014/0079832 A1 | 3/2014 | Heaton et al. | |
| 2014/0080887 A1 | 3/2014 | Heaton et al. | |
| 2014/0080888 A1 | 3/2014 | Heaton et al. | |

FOREIGN PATENT DOCUMENTS

| | | | |
|---|---|---|---|
| CN | 1243745 A | * | 2/2000 |
| GB | 9822333 | * | 12/1998 |
| KR | 1020000000757 A | | 1/2000 |
| RU | 2429001 C1 | * | 9/2011 |
| WO | 9528854 A2 | | 11/1995 |
| WO | 2004112511 A2 | | 12/2004 |
| WO | WO 2007095618 A3 | * | 10/2007 |

OTHER PUBLICATIONS

"MayoClinic". Post-traumatic stress disorder (PTSD). Web Publication Date: Apr. 8, 2011 [Retrieved from the Internet on: Apr. 10, 2013]. Retrieved from: <URL: http://www.mayoclinic.com/health/post-traumatic-stress-disorder/DS00246/DSECTION=treatments-and-drugs>.*

Sahley, B J. "Amino Acid Brain Boosters" from teenlinkusa. Internet Archive Date: May 25, 2010 [Retrieved from the Internet on: Apr. 9, 2013]. Retrieved from the Internet: <URL: http://web.archive.org/web/20100525114105/http://www.teenlinkusa.com/aminoacids2.html>.*

Grioli et al. "Pyroglutamic acid improves the age associated memory impairment". citation and abstract from Pyroglutamate. Internet Archive Date: Jun. 13, 2002. Retrieved from the Internet on Apr. 9, 2013. Retrieved from: <URL: http://web.archive.org/web/20020613031716/http://www.raysahelian.com/pyroglutamate.html>.*

Farr et al. J Neurochem. Mar. 2003;84(5):1173-1183.*

King, J. "What is L-Arginine HCl?". Web Publication Date: Jun. 6, 2011. Retrieved from the Internet on: Apr. 9, 2013]. Retrieved from: <URL: http://web.archive.org/web/20020613031716/http://www.raysahelian.com/pyroglutamate.html>.*

"L-Lysine" from IronMagazine.com. Posting date: 2011—[Retrieved from the Internet on: Apr. 9, 2013]. Retrieved from. <URL: http://www.ironmagazineforums.com/supplements/149021-l-lysine.html>.*

"Helpguide.org". Retrieved from the internet on: Feb. 5, 2014. Retrieved from: <URL: http://www.helpguide.org/life/sleep_disorders.htm>.*

"Sleep Disorders". Retrieved from the Internet on: Feb. 5, 2014. Retrieved from: <URL:http://www.healthline.com/health/sleep/disorders>.*

"MedlinePlus: L-arginine". Internet Archive Date: Oct. 5, 2010 [Retrived from the Internet on: Jul. 31, 2014]. Retrieved from: <URL: http://www.nlm.nih.gov/medlineplus/druginfo/natural/875.html>.*

Brigitte Mars. Internet Publication Date: Mar. 1, 2009 [Retrieved from the Internet on: Jul. 31, 2014]. Retrieved from: <URL: http://brigittemars.com/articles/herbal-natural-remedies/treating-headaches-naturally/>.*

(Continued)

*Primary Examiner* — Amy L Clark

(74) *Attorney, Agent, or Firm* — TraskBritt

(57) ABSTRACT

Embodiments herein relate to nutritional supplements for treating post-traumatic stress disorder in human beings, and to methods of using the same. In particular examples, the nutritional supplement comprises an amino acid secretagogue composition.

16 Claims, 2 Drawing Sheets

(56) References Cited

OTHER PUBLICATIONS

Bae, O.; "A Chinese medicinal composition for stimulating growth hormone", KR 2000/000757 A, 2000, Abstract Only.
Boger, R. H., "The Pharmacodynamics of L-Arginine1-3", The Journal of Nutrition: 6th Amino Acid Assessment Workshop, 2007, pp. 1650S-1655S, vol. 137, American Society for Nutrition.
Chowen et al.; The regulation of GH secretion by sex steroids; European Journal of Endocrinology, 2004, pp. U95-U100, vol. 151, Society of the European Journal of Endocrinology.
Collier, S. R. et al., "Growth hormone responses to varying doses of oral arginine", Growth Hormone & IGF Research, 2005, vol. 15, pp. 136-139.
Cooper et al.; "Subclinical thyroid disease," Jan. 23, 2012, 13 pages.
Devesa et al.; "The Role of Sexual Steroids in the Modulation of Growth Hormone (GH) Secretion in Humans," J. Steroid Biochem. Molec. Biol., 1991,vol. 40—No. 1-3, pp. 165-173.
"External Wind", <http://www.tcvmherbal.com/JTDocs/Flyers/External%20Wind.pdf>, Downloaded from website Oct. 22, 2013, Jing Tang, 2 pages.
Gasco et al.; "Retesting the childhood-onset GH-deficient patient," European Journal of Endocrinology, vol. 159, 2008, pp. S45-S52.
Fung, et al; "Schizonepeta tenuifolia: Chemistry, Pharmacology, and Clinical Applications," J. Clin. Pharmacal., 2002, vol. 42, pp. 30-36.
Yen et al.; "Aging and the Adrenal Cortex," Experimental Gerontology, vol. 33, Nos. 7/8, pp. 897-910, 1998.
Goto et al.; "Growth Hormone Receptor Antagonist Treatment Reduces Exercise Performance in Young Males", Sep. 2009, J Clin Endocrinol Metab, 94(9), pp. 3265-3272.
Tarantini et al.; "Serum ghrelin levels in growth hormone-sufficient and growth hormone-deficient patients during growth hormone-releasing hormone plus arginine test," J. Endocrinol. Invest. vol. 32, pp. 335-337, 2009.
Grunfeld et al.; "The Acute Effects of Human Growth Hormone Administration on Thyroid Function in Normal Men*," Journal of Clinical Endocrinology and Metabolism, 1988, vol. 67—No. 5, pp. 1111-1114.
Hansen et al.; Effects of 2 wk of GH administration on 24-h indirect calorimetry in young, healthy, lean men; Am. J. Physiol Endocrinol Metab 289: E1030-E1038, 2005.
Ho et al.; "The Pharmacokinetics, Safety and Endocrine Effects of Authentic Biosynthetic Human Growth Hormone in Normal Subjects", Clinical Endocrinology, 1989, vol. 30, pp. 335-345.
Yuen et al.; "Is Lack of Recombinant Growth Hormone (GH)-Releasing Hormone in the United States a Setback or Time to Consider Glucagon Testing for Adult GH Deficiency?", J. Clin, Endocrinol Metab, Aug. 2009, vol. 94—No. 8, pp. 2702-2707.
Leelarungrayub et al.; "N-Acetylcysteine Supplementation Controls Total Antioxidant Capacity, Creatine Kinase, Lactate, and Tumor Necrotic Factor-Alpha against Oxidative Stress Induced by Graded Exercise in Sedentary Men," Oxidative Medicine and Cellular Longevity. vol. 2011, Article ID 329643, 7 pages.
Weizman et al.; "Impact of the Gulf War on the Anxiety, Cortisol, and Growth Hormone Levels of Israeli Civilians," Am J. Psychiatry, vol. 151—No. 1, Jan. 1994, pp. 71-75.
Maggi et al.; "Hormonal Causes of Male Sexual Dysfunctions and Their Management (Hyperprolactinemia, Thyroid Disorders, GH Disorders, and DHEA)," International Society for Sexual Medicine, 2012, 9 pages.
Weikel et al.; "Ghrelin promotes slow-wave sleep in humans," Am J. Physiol Endocrinol Metab, vol. 284, pp. E407-E415, 2003.
Millea, P. J.; "N-Acetylcysteine: Multiple Clinical Applications," American Family Physician, Aug. 1, 2009, vol. 80—No. 3, pp. 265-269.
Moller et al.; "Effects of Growth Hormone Administration on Fuel Oxidation and Thyroid Function in Normal Man," Metabolism, vol. 41—No. 7, Jul. 1992, pp. 728-731.
Oliveira, et al.; "Free Amino Acids of Tronchuda Cabbage (Brassica oleracea L. var. costata DC): Influence of Leaf Position (Internal or External) and Collection time", Journal of Agricultural and Food Chemistry, 2008, vol. 56, pp. 5216-5221.
Silber et al.; "Growth and Maintenance of Dogs Fed Amino Acids as the Source of Dietary Nitrogen," The Journal of Nutrition, Oct. 11, 1948, pp. 429-441.
Pryor, et al.; "Growth Hormone: Amino Acids as GH secretagogues," <http://www.vrp.com/amino-acids/amino-acids/growth-hormone-amino-acids-as-gh-secretagogues-a-review-of-the-literature>, Retrieved Jul. 16, 2014, 5 pages.
Pavel et al.; "Impact of Growth Hormone on Central Nervous Activity, Vigilance, and Tiredness after Short-Term Therapy in Growth Hormone-Deficient Adults," Horm. Metab. Res., 2003, vol. 35, pp. 114-119.
PCT Search Report for International application No. PCT/US2013/060672, dated Dec. 2, 2013, 4 pages.
Pradines-Figueres et al.; "Transcriptional control of the expression of lipoprotein lipase gene by growth hormone in preadipocyte Ob1771 cells," Journal of Lipid Research, vol. 31, 1990, pp. 1283-1291.
Reid et al.; "N-Acetylcysteine Inhibts Muscle Fatigue in Humans," J. Clin. Invest., vol. 94, Dec. 1994, pp. 2468-2474.
Van Liempt et al.; "Decreased nocturnal growth hormone secretion and sleep fragmentation in combat-related posttraumatic stress disorder; potential predictors of impaired memory consolidation," Psychoneuroendocrinology, 2011, vol. 36, pp. 1361-1369.
Rudman et al.; "The Short Child with Subnormal Plasma Somatomedin C1," Pediatric Research, vol. 19—No. 10, 1985, pp. 975-980.
Russell et al.; "Free Triiodothyronine has a distinct circadian rhythm that is delayed but parallels thyrotropin levels," J. Clin Endocrin Metab., Mar. 25, 2008, 22 pages.
Vermeulen et al., "Testosterone, body composition and aging," J. Endocrinol. Invest., vol. 22, pp. 110-116, 1999.
Salomon et al.; "The Effects of Treatment with Recombinant Human Growth Hormone on Body Composition and Metabolism in Adults with Growth Hormone Deficiency," New England Journal of Medicine, Dec. 28, 1998, vol. 321—No. 26, pp. 1797-1803.
"Schizonepeta Tenuifolia," <http://examine.com/supplements/Schizonepeta+tenuifolia/>, Sep. 30, 2013, 12 pages.
Schwartz et al., "Hormone Replacement Therapy in the Geriatric Patient: Current State of the Evidence and Questions for the Future. Estrogen, Progesterone, Testosterone, and Thyroid Hormone Augmentation in Geriatric Clinical Practice: Part 1," Clin Geriatr Med vol. 27, 2011, pp. 541-559.
Schwartz et al., "Hormone Replacement Therapy in the Geriatric Patient: Current State of the Evidence and Questions for the Future. Estrogen, Progesterone, Testosterone, and Thyroid Hormone Augmentation in Geriatric Clinical Practice: Part 2," Clin Geriatr Med, vol. 27, 2011, pp. 561-575.
Sen et al.; "Exercise-induced oxidative stress: glutathione supplementation and deficiency," J. Appl. Physiol., vol. 77, 1994, pp. 2177-2187.
Sen et al.; "Oxidative stress after human exercise: effect of N-acetylcysteine supplementation," J. Appl. Physiol., vol. 76, 1994, pp. 2570-2577.
Sen, C. K.; "Glutathione homeostasis in response to exercise training and nutritional supplements," 1999, Molecular and Cellular Biochemistry, vol. 196, pp. 31-42.
Sevigny et al.; "Growth hormone secretagogue MK-677: No clincical effect on AD progression in a randomized trial," American Academy of Neurology, 2008, vol. 71, pp. 1702-1708.
Welbourne, T. C.; "Increased plasma bicarbonate and growth hormone after an oral glutamine load 81-3," The American Journal of Clinical Nutrition, 1995, vol. 61, pp. 1058-1061.
Tavakkolizadeh et al.; "Effect of Growth Hormone on Intestinal Na+/Glucose Cotransporter Activity," Journal of Parenteral and Enteral Nutrition, vol. 25, No. 1, Mar. 2000, pp. 18-22.
Topo et al.; "The role and molecular mechanism of D-aspartic acid in the release and synthesis of LH and testosterone in humans and rats," Reproductive Biology and Endocrinology, Oct. 27, 2009, 11 pages.
Van Cauter et al.; "Metabolic consequences of sleep and sleep loss," Sleep Medicine 9 Suppl. 1, 2008, pp. S23-S28.
Kim et al.; "Anti-Inflammatory Activity of Schizonepeta tenuifolia through the Inhibition of MAPK Phosphorylation in Mouse

(56) References Cited

OTHER PUBLICATIONS

Peritoneal Macrophages," The American Journal of Chinese Medicine, vol. 36—No. 6, 2008, pp. 1145-1158.
Anonymous, "Dr. Oz Human Growth Hormone HGH the Pursuit of Youth and Beauty," Oct. 13, 2011, retrieved from the internet: URL:http://healthybodydaily.com/dr-oz-in-case-you-missed-it/dr-oz=hgh-human-growth-hormone (retrieved on Sep. 15, 2014).
Anonymous, "Animal Outreach," Aug. 18, 2012, retrieved from the internet: URL: http://animal-outreach.org/2012/08 (retrieved on Sep. 15, 2014).
Alba-Roth et al.; Arginine Stimulates Growth Hormone Secretion by Suppressing Endogenous Somatostatin Secretion; Journal of Clinical Endocrinology and Metabolism, vol. 67, No. 6, 1988; 1186-1189.
Albert et al.; Low-Dose Recombinant Human Growth Hormone as Adjuvant Therapy of Lifestyle Modifications in the Management of Obesity; Journal of Clinical Endocrinology & Metabolism 89(2) 695-704; 2004.
Bernardi et al.; Somatotropic axis and body weight in pre-menopausal and post-menopausal women: evidence for a neuroendocrine derangement, in absence of changes of insulin-like growth factor binding protein concentrations; Human Reproduction vol. 12, No. 2 pp. 279-287, 1998.
Bidlingmaier et al.; Growth Hormone; Handbook of Experimental Pharmacology 195; 2010; pp. 187-200.
Bjorntorp, et al.; Hypothalamic Origin of the Metabolic Syndrome X; Annals New York Academy of Sciences, pp. 297-307; 1999.
Bjorntorp, P.; Do Stress reactions cause abdominal obesity and comorbidities?; The International Association for the Study of Obesity, Obesity reviews; 2 73-85; 2001.
Bjorntorp, P.; The regulation of adipose tissue distribution in humans; International Journal of Obesity (1996) 20, 191-302.
Blackman et al.; Growth Hormone and Sex Steroid Administration in Healthy Aged Women and Men A Randomized Controlled Trial; JAMA, Nov. 12, 2002 vol. 288, No. 18; pp. 2282-2292.
Bredella, et al.; Peak Growth Hormone-Releasing Hormone-Arginine-Stimulated Growth Hormone is Inversely Associated with Intramyocellular and Intrahepatic Lipid Content in Premenopausal Women with Obesity; J. Clin Endrocrinol Metab. Oct. 2009; 94(10): 3995-4002.
Carli et al.; Changes in the exercise-induced hormone response to branched chain amino acid administration; Eru. J. Appl. Physiology (1992) 64:272-277.
Chromiak et al.; Use of Amino Acids as Growth Hormone-Releasing Agents by Athletes; Nutrition 18:657-661, 2002.
Corpas et al.; Human Growth Hormone and Human Aging; Endocrine Reviews, vol. 14, No. 1; 1993; pp. 20-39 111.
Corpas et al.; Oral Arginine-Lysine Does not Increase Growth Hormone or Insulin-like Growth Factor-I in Old Men; Journal of Gerontology: 1993, vol. 48, No. 4, M128-M133.
Ding et al.; Novel serum protein biomarkers indicative of growth hormone doping in healthy human subjects; Preteomics 2011, 11, 3565-3571.
Fogelholm et al. Low-Dose Amino Acid Supplementation: No Effects on Serum Human Growth Hormone and Insulin in Male Weightlifters; International Journal of Sport Nutrition, 1993, 3, 290-297.
Gourmelen et al., Effet du chlorhydrate' ornithine sur le taux plamatique de'hormone de croissance (HGH); Annels D'Endocrinologie; pp. 526-528; 1972.
Hayes et al.; Recombinant Human Growth Hormone and Recombinant Human Insulin-Like Growth Factor I Diminish the Cataboloic Effects of Hypogonadism in Man: Metabolic and Molecular Effects; The Journal of Clinical Endocrinology & Metabolism; vol. 86, No. 5; 2001.
Hersch et al.; Growth hormone (GH)-releasing hormone and GH secretagogues in normal aging: Fountain of Youth or Pool of Tantalus?; Clinical Interventions in Aging 2008:3(1) 121-129.
Iranmanesh et al., Age and Relative Adiposity are Specific Negative Determinants of the Frequency and Amplitude of Growth Hormone (GH) Secretory Bursts and the Half-Life of Endogenous GH in Healthy Men; Journal of Clinical Endocrinology and Metabolism; vol. 73, No. 5; pp. 1081-1088 1991.
Isidori et al.; A Study of growth hormone release in man after oral administration of amino acids; Current Medical Research and Opinion; vol. 7, No. 7, 1981; pp. 475-481.
Karlsson et al.; Effects of growth hormone treatment on the leptin system and on energy expenditure in abdominally obese men; European Journal of Endocrinology (1998) 138 408-414.
Kraemer et al.; Chronic Resistance training in women potentiates growth hormone in vivo bioactivity: characterization of molecular mass varients; Am. J. Physiol Endocrinol Metab 291: E1177-E1187, 2006.
Lambert et al.; Failure of Commercial Oral Amino Acid Supplements to Increase Serum Growth Hormone Concentrations in Male Body-Builders; International Journal of Sport Nutrition, 1993, 3, 298-305.
Legakis et al.; Human Galanin Secretion is Increased Upon Normal Exercise Test in Middle-Age Individuals; Endocrine Research 26(3), 357-365 (2000).
Maccario et al.; Relationships between IFG-I and age, gender, body mass, fat distribution, metabolic and hormonal variables in obese patients; International Journal of Obesity (1999) 23, 612-618.
Makimura et al.; The relationship between reduced testosterone, stimulated growth hormone secretion and increased carotid inima-media thickness in obese men; Clin Endocrinol (Oxf). Nov. 2010; 73(5): 622-629.
Menagh et al.; Growth Hormone Regulates the Balance Between Bone Formation and Bone Marrow Adiposity; JBMR; vol. 25, No. 4, Apr. 2010, pp. 757-768.
Merimee et al.; Arginine-Initiated Release of Human Growth Hormone; The New England Journal of Medicine; Jun. 26, 1969; pp. 1434-1438.
Nindl et al.; Growth hormone pulsatility profile characteristics following acute heavy resistance exercise; J. Appl Physiol 91: 163-172, 2001.
O'Connor et al.; Interrelationships of Spontaneous Growth Hormone Axis Activity, Body Fat, and Serum Lipids in Healthy Elderly Women and Men; Metabolism, vol. 48, No. 11 (Nov.), 1999: pp. 1424-1431.
Papadakis et al.; Effect of growth hormone replacement on wound healing in healthy older men; Would Repair and Regeneration Oct.-Dec. 1996; pp. 421-425.
Papadakis et al.; Growth Hormone Replacement in Healthy Older Men Improves Body Composition but Not Functional Ability; Ann Intern Med. 1996; 124-: 708-716.
Pasquali et al.; Hormones and pathophysiology of obesity; Hormones and Obesity; 2001 pp. 9-20.
Pelsers et al.; Influence of Gender in Growth Hormone Status in Adults: Role of Urinary Growth Hormone; Clinical Chemistry 45, No. 3, 1999, pp. 443-444.
Perry, Horace M. III; The Endocrinology of Aging; Clinical Chemistry 45:8(B); 1369-1376 (1999).
Rubin et al.; New anabolic therapies in osteoporosis; Current Opinon in Reeumatology 2002, 14:433-440.
Rudman et al.; Effects of Human Growth Hormone in Men over 60 Years Old; The New England Journal of Medicine; vol. 323, Jul. 5, 1990; 6 pages.
Su et al.; Insulin-like growth factor 1 and hair growth; 1999 Dermatology Online Journal; 20 pages.
Suminski et al.; Acute Effect of Amino Acid Ingestion and Resistance Exercise on Plasma Growth Hormone Concentration in Young Men; International Journal of Sport Nutrition, 1997, 7, 48-60.
Twickler et al.; Adult-Onset Growth Hormone Deficiency: Relation of Postprandial Dyslipidemia to Premature Atherosclerosis; The Journal of Clinical Endocrinology & Metabolism 88(6): 2479-2488 2003.
Vance, Mary L.; Growth Hormone for the Elderly?; The New England Journal of Medicine; Jul. 5, 1990; pp. 52-54.
White et al.; Effects of an Oral Growth Hormone Secretagogue in Older Adults; J. Clin Endocrin Metab.; 2009; 29 pages.
Zouboulis et al.; Intrinsische Hautalterung; Eine kritische Bewertung der Rolle der Hormone; Hautarzt 2003 54: 825-832.

* cited by examiner

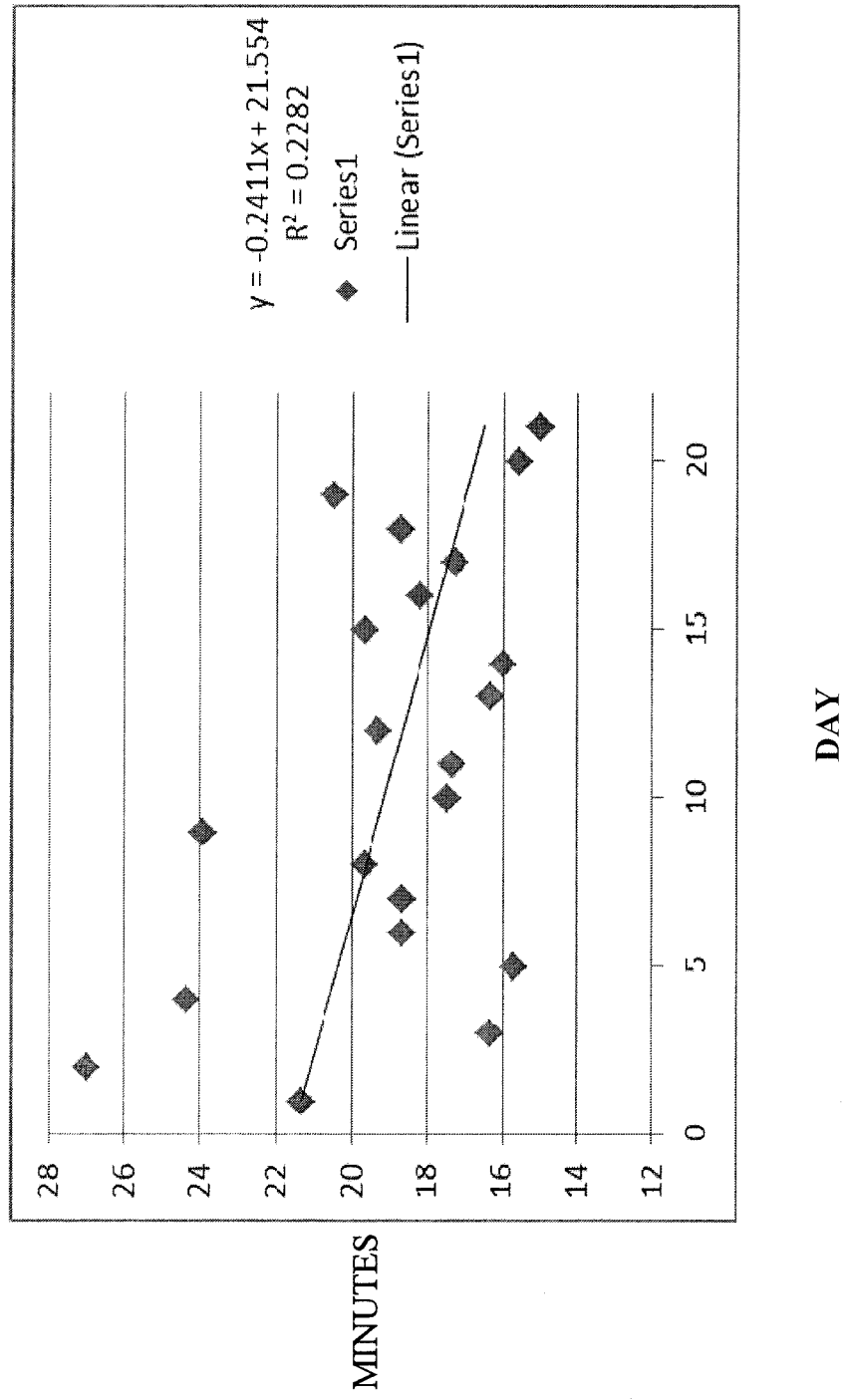
Figure 1: Time to fall asleep

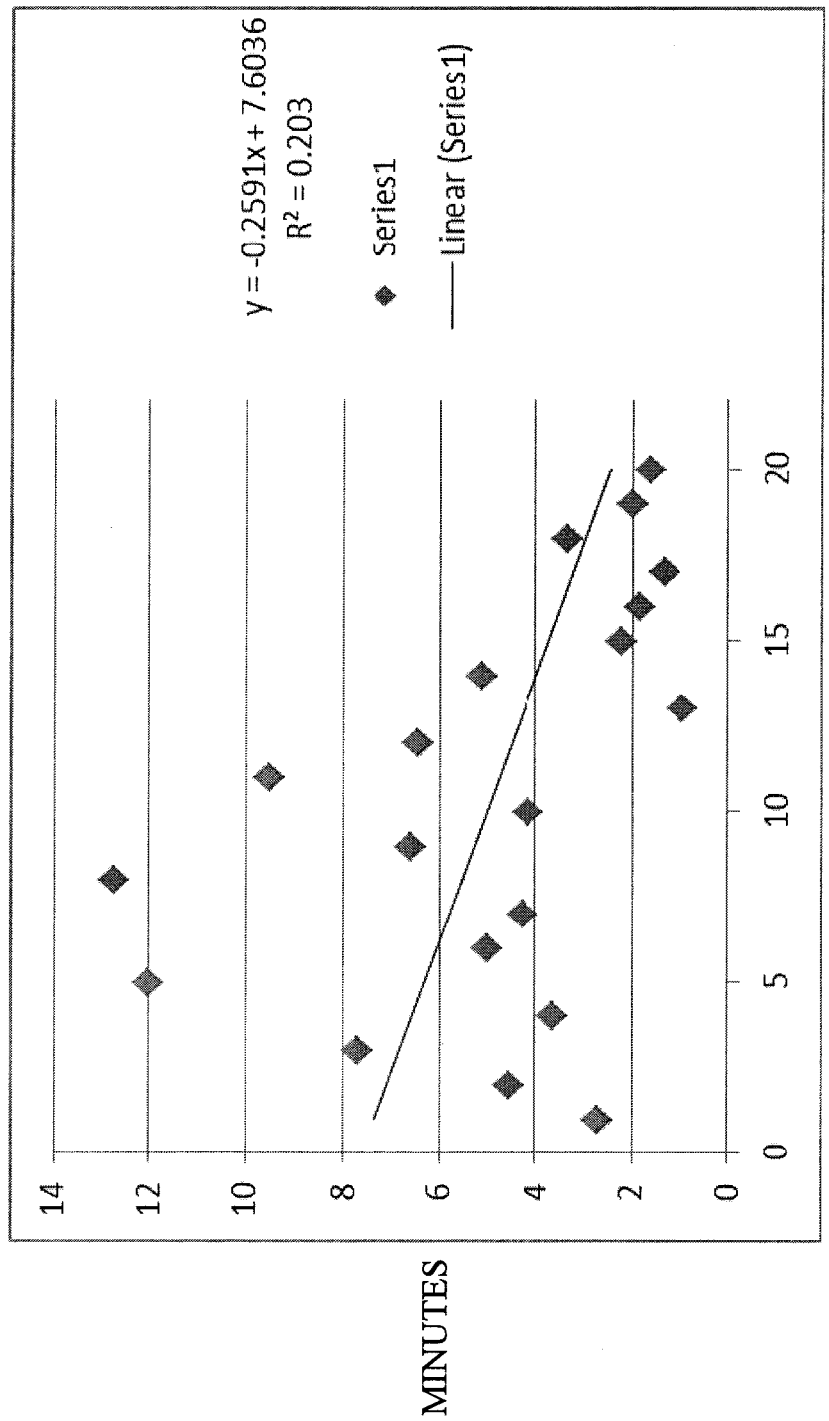
Figure 2: Time awake during sleep

METHODS FOR TREATING POST-TRAUMATIC STRESS DISORDER

TECHNICAL FIELD

Embodiments of the invention generally relate to methods and supplements for treating post-traumatic stress disorder.

BACKGROUND

Posttraumatic stress disorder (PTSD) is a severe anxiety disorder that can develop after exposure to any event that results in psychological trauma. This event may involve the threat of death to oneself or to someone else, typically overwhelming the individual's ability to cope. As an effect of psychological trauma, PTSD is less frequent and more enduring than the more commonly seen acute stress response. Diagnostic symptoms for PTSD include re-experiencing the original trauma(s) through flashbacks or nightmares, avoidance of stimuli associated with the trauma, and increased arousal—such as difficulty falling or staying asleep, anger, and hypervigilance.

Posttraumatic stress disorder is classified as an anxiety disorder, characterized by aversive anxiety-related experiences, behaviors, and physiological responses that develop after exposure to a psychologically traumatic event (sometimes months after). Its features persist for longer than 30 days, which distinguishes it from the briefer acute stress disorder. These persisting posttraumatic stress symptoms cause significant disruptions of one or more important areas of life function.

Although most people (50-90%) encounter trauma over a lifetime, only about 8% develop full PTSD. Vulnerability to PTSD is believed to stem from an interaction of biological diathesis, early childhood developmental experiences, and trauma severity.

A variety of medications has shown adjunctive benefit in reducing PTSD symptoms, but there is no clear drug treatment for PTSD. Positive symptoms (re-experiencing, hypervigilance, increased arousal) generally respond better to medication than negative symptoms (avoidance, withdrawal), and it is recommended that any drug trial last for at least 6-8 weeks.

Medication classes that have been used for symptom management include: SSRIs (selective serotonin reuptake inhibitors, such as citalopram, escitalopram, fluoxetine, fluvoxamine, paroxetine, and sertraline); anti-depressants (such as, bupropion, venlafaxine, sertraline, fluoxetine, nefazodone, heterocyclics, and paroxetine); alpha-adrenergic antagonists (such as prazosin and clonidine); anti-convulsants, mood stabilizers, anti-aggression agents (such as carbamazepine, zolpidem, lamotrigine, valproic acid, and buspirone); antipsychotics; atypical antidepressants (such as nefazodone and trazodone); beta blockers; benzodiazepines; glucocorticoids; heterocyclic/tricyclic anti-depressants (such as amitriptyline and imipramine); and monoamine-oxidase inhibitors (MAOIs). Medication classes that have been used for symptom prevention include: alpha-adrenergic antagonists; beta blockers; and glucocorticoids.

A direct correlation has been observed between low growth hormone curves at onset of sleep and sleep problems in PTSD. (See, e.g., van Liempt, Decreased nocturnal growth hormone secretion and sleep fragmentation in combat-related posttraumatic stress disorder; potential predictors of impaired memory consolidation, Psychoneuroendocrinology (2011) 36, 1361-1369).

It would be desirable to provide a nutritional supplement for treating post-traumatic stress disorder.

BRIEF SUMMARY OF THE INVENTION

Described herein are nutritional supplement and method of using the same. The nutritional supplement includes an amino acid secretagogue composition, which, taken orally, stimulates the pituitary gland to release hGH.

Some embodiments include an oral nutritional supplement that comprises L-arginine, oxo-proline, and L-lysine.

A particular embodiment of the present disclosure relates to an oral nutritional supplement that includes the amino acids l-lysine, l-arginine, oxo-proline, and one of either cysteine or glutamine. The amino acids may be delivered as non-toxic salts thereof, effective complexes thereof, stable chelates thereof, active esters thereof, functional derivatives thereof, and mixtures thereof which are effective to increase hGH levels in the general population.

Another particular embodiment relates to an oral nutritional supplement that consists essentially of l-lysine HCl, l-arginine HCl, oxo-proline, N-acetyl-l-cysteine, l-glutamine, and schizonepeta (aerial parts) powder.

Other embodiments are drawn to methods of treating post-traumatic stress disorder in humans that include orally administering the disclosed nutritional supplement to a human being suffering from post-traumatic stress disorder.

BRIEF DESCRIPTION OF THE FIGURES

FIG. 1 shows a linear regression analysis of time to fall asleep with continued use of the supplement over time; and FIG. 2 shows time awake during sleep over time with continued use of the supplement.

DETAILED DESCRIPTION OF THE INVENTION

The present invention relates to a nutritional supplement for use by a human being. The present invention is drawn to a nutritional supplement and method of using the same. The nutritional supplement is an amino acid secretagogue composition, which, taken orally, treats one or more post-traumatic stress disorder (PTSD) symptoms. The supplement of the present invention works as a dietary supplement by assisting the body's own ability to treat PTSD symptoms naturally in a manner which is safe and effective, as well as being affordable.

A particular embodiment of the present disclosure relates to an oral nutritional supplement that includes l-lysine, l-arginine, oxo-proline, and one of either cysteine or glutamine. The supplement may additionally include both cysteine and glutamine and/or schizonepeta powder. In particular embodiments, a functional dosage includes the l-arginine at a level between 0.1-6 mmol and the oxo-proline between 0.1-8 mmol, and/or the l-lysine in an amount between 0.1-12 mmol. The cysteine and/or glutamine may be contained at a level between 0.001-6 mmol. In another particular embodiment, a functional dosage includes the l-arginine at a level between 2.5-4.5 mmol and the oxo-proline between 4-6 mmol, and/or the l-lysine in an amount between 7-9 mmol. The cysteine and/or glutamine may be contained at a level between 0.001-0.5 mmol. The cysteine can be n-acetyl L-cysteine and the glutamine may be l-glutamine. The amino acids may be delivered as non-toxic salts thereof, effective complexes thereof, stable chelates thereof, active esters thereof, functional derivatives thereof, and mixtures thereof which are effective to increase hGH levels in the general population. The nutritional supplement may be present in an amount of 2.9 grams. The nutritional supplement may be in any acceptable and known oral formulation, such as powder, tablet, capsule, liquid, or wafer form.

Another particular embodiment relates to an oral nutritional supplement that consists essentially of l-lysine HCl, l-arginine HCl, oxo-proline, N-acetyl-l-cysteine, l-glutamine, and schizonepeta (aerial parts) powder. In particular embodiments, a functional dosage includes the l-arginine HCl at a level between 0.1-6 mmol and the oxo-proline between 0.1-8 mmol, and/or the l-lysine HCl in an amount between 0.1-12 mmol. The n-acetyl L-cysteine and/or l-glutamine may be contained at a level between 0.001-6 mmol. In another particular embodiment, a functional dosage includes the l-arginine HCl at a level between 2.5-4.5 mmol and the oxo-proline between 4-6 mmol, and/or the l-lysine HCl in an amount between 7-9 mmol. The n-acetyl L-cysteine and/or l-glutamine may be contained at a level between 0.001-0.5 mmol. The nutritional supplement may be in any acceptable and known oral formulation, such as powder, tablet, capsule, liquid, or wafer form.

Other embodiments are drawn to methods of increasing human growth hormone in humans that include orally administering the disclosed nutritional supplement to a healthy human being. As used herein, "healthy human being" means a human being without any physiological deficiency in hGH independent of age. Particular embodiments of the invention relate to oral administration of the disclosed nutritional supplement to a human that is at least 30 years old. The nutritional supplement may be administered from one to three times daily or, alternatively, may be administered every other day, or may be administered once a week. In particular embodiments, the nutritional supplement may be administered on an empty stomach.

In accordance with the "consist essentially of" and "consisting essentially of" language, the nutritional supplement of the third embodiments is essentially limited to the aforementioned ingredients and does not include any additional active ingredients intended to add nutritional content (e.g., vitamins, minerals, etc.), but may include additional ingredients not intended to add nutritional content such as ingredients intended to fulfill a non-nutritional purpose (e.g., coloring, fillers, flavoring, an ingredient for maintaining the structural form, etc.).

Each ingredient of the nutritional supplement of the present invention may be prepared in accordance with any method known to one of ordinary skill in the art. Alternatively, each ingredient may be obtained in a fully prepared from a commercially available source.

The nutritional supplement of the present invention may be in any suitable oral administration form, including but not limited to: a chewable form, a liquid form, a spray form, a capsule form, a suppository form, dissolvable wafer, and a powder form.

Irrespective of the structural form of the nutritional supplement, the ingredients of the nutritional supplement may be distributed homogeneously or non-homogeneously within the nutritional supplement.

The nutritional supplement of the present invention may be ingested on a regular basis, such as a daily or weekly intake at a dosage tailored to an individual's needs; i.e., the nutritional supplement is to be taken regularly as multiples (1×, 2×, etc.) of the structural units (pills, tablets, capsules, liquid dose, etc.) in accordance with the needs of the individual. For example, a senior citizen leading a sedentary life may need higher daily doses than does a young person engaged in regular strenuous exercise (e.g., a weight lifter). Alternatively, the nutritional supplement of the present invention may be ingested on an as-needed basis at a dosage tailored to the individual's needs. Medical or nutritional counseling may be beneficial for arriving at a desirable or optimal dosage tailored to the individual's needs.

The combination of types of amino acids, mass ranges, and specific formulations have been selected to be synergistically balanced and of adequate quantity to achieve the desired physiological effect, namely, treatment of PTSD symptoms. Improper combinations of the amino acids may be ineffective. The component amino acids are synergistic in the sense that several of them when combined together, synergistically treat one or more symptoms of PTSD. The combination was also chosen to reduce or inhibit chemical combination or reaction between the amino acids.

EXAMPLES

Example 1

A double-blind clinical study involved 15 healthy subjects [10 males, 5 females; mean age=33±7 years]. Each subject completed a baseline Epworth Sleepiness Scale self-report questionnaire and a standardized assay of usual sleep habits. All subjects were deemed to have average sleep parameters within a normal range.

The subjects were then provided a three week supply of a novel supplement SeroVital (2.9 g/dose blend of l-lysine HCl, l-arginine HCl, oxo-proline, N-acetyl-l-cysteine, l-glutamine, and schizonepeta (aerial parts) powder). The novel SeroVital blend has been shown previously to increase serum human growth hormone hGH levels by 8 times (equivalent to 682%) 120 minutes after a single dose in healthy male and female volunteers. Because night-time onset of hGH has been directly correlated to sleep efficiency, we investigated sleep patterns with continued use of the supplement when taken on an empty stomach, two hours after dinner prior to bedtime, every night for three weeks. On each trial day, subjects reported 1) time went to bed; 2) time of final wakening; 3) estimated time to fall asleep; 4) time of awakening during sleep/length of time awake. Data was compiled by day for estimated time to fall asleep and length of time awake during sleep in order to assess sleep efficiency. Daily values for each measure were plotted as an average (±S.D.) among the subjects over the time course of the study, and a linear regression was tabulated to assess overall trends over time. All available data was included in the analysis.

Linear regression analysis showed that both estimated time to fall asleep (FIG. 1) and time awake during sleep (FIG. 2) tended to decrease over time with continued use of the supplement over the time course of the study. Time to fall asleep decreased with an average slope of −0.24 min/day, and time awake during sleep decreased by an average slope of −0.26 min/day. Overall, these results so a trend towards greater sleep efficiency by measurements of both time to fall asleep and time awake during sleep, both with a quantified average decrease of about 0.25 min/day over three weeks with regular nighttime use of the novel SeroVital supplement (when taken as directed, on an empty stomach, two hours after dinner prior to bedtime).

Example 2

Veterans with PTSD are recruited through outpatient clinics and Veteran Affairs Medical Centers. Trauma controls (TC; veterans without PTSD) and healthy controls (HC; service members never deployed or civilians) are recruited through advertisements. Controls are matched with the PTSD group for age, year of deployment (TC), and region of deployment (TC). All participants are screened for psychiatric illness. The diagnosis of PTSD is confirmed by the Clinician Administered PTSD Scale (CAPS) and patients are included when a score of over 50 is obtained and there is an absence of psychiatric disorders other than mood and anxiety disorder. TCs are included when they meet the criteria for PTSD (experienced, witness, or was confronted with an event involving actual or threatened death or serious injury to self or others), but has a CAPS score below 18. All participants are medically healthy individuals and are free from psychotropic medication and alcohol or drug dependence in the past six months. All control subjects are without without a history of psychiatric disorders and without sleep complaints.

Sleep registrations during two consecutive nights are conducted in a sleep laboratory. Sleep recordings are acquired, including bipolar derivations of EMG, EOG for vertical and horizontal eye movements, EEG, and ECG.

To assess declarative memory consolidation, a 15 word task is administered three hours before sleep on the second evening. Fifteen neutral one syllable words are visually presented on a computer screen, and repeated three times. Every presentation is followed by a free immediate recall and is assessed the next morning between 30-45 minutes after awakening.

Sleep data are analyzed in 30 second epochs by an experienced sleep technician who is blind to PTSD diagnosis. The number of spontaneous awakenings for Stage 2 sleep, slow wave sleep, or rapid eye movement sleep are determined for the first half of the night. Total sleep time is also determined.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. A method of improving sleep and enhancing memory in a subject in need thereof, the method comprising:
   orally administering a nutritional supplement composition in unit dosage form to the subject, wherein the unit dosage consists of:
   0.1 to 6 mmol L-arginine;
   0.1 to 8 mmol Oxo-proline;
   0.1 to 12 mmol L-lysine;
   0.001 to 6 mmol N-acetyl L-cysteine; and
   0.001 to 6 mmol L-glutamine.

2. The method of claim 1, wherein the L-arginine is L-arginine HCl salt, or L-lysine is L-lysine HCl salt, or both.

3. The method of claim 1, wherein the unit dosage form has a mass of 2.9 grams.

4. The method of claim 1, wherein the unit dosage form is a powder, tablet, capsule, liquid, or wafer.

5. The method of claim 1, wherein the unit dosage form is administered to the subject from one to three times daily.

6. The method of claim 1, wherein the unit dosage form is administered to the subject once a week.

7. The method of claim 1, wherein the unit dosage form is administered to the subject on an empty stomach.

8. The method of claim 1, wherein the subject is a female.

9. The method of claim 1, wherein the subject exhibits one or more of: re-experiencing an original trauma through flashbacks or nightmares, avoidance of stimuli associated with an original trauma, increased arousal, difficulty falling or staying asleep, anger, and hypervigilance.

10. A method for improving sleep in a human subject in need thereof, the method comprising:
    orally administering a nutritional supplement composition in unit dosage form to the human subject, wherein the unit dosage consists of:
    0.1 to 6 mmol L-arginine;
    0.1 to 8 mmol Oxo-proline;
    0.1 to 12 mmol L-lysine;
    0.001 to 6 N-acetyl L-cysteine;
    0.001 to 6 L-glutamine; and
    about 125 µg Schizonepeta aerial parts powder.

11. The method of claim 10, wherein the nutritional supplement is provided in an amount of 2.9 grams.

12. The method of claim 10, wherein the nutritional supplement is provided in powder, tablet, capsule, liquid, or wafer form.

13. The method of claim 10, wherein the nutritional supplement is administered from one to three times daily.

14. The method of claim 10, wherein the nutritional supplement is administered once a week.

15. The method of claim 10, wherein the nutritional supplement is administered on an empty stomach.

16. The method of claim 10, wherein the subject is female.

* * * * *